United States Patent [19]

Thomasen et al.

[11] Patent Number: 4,867,797

[45] Date of Patent: Sep. 19, 1989

[54] METHOD FOR CLEANING INSTRUMENTS USED FOR ANALYZING PROTEIN-CONTAINING BIOLOGICAL LIQUIDS

[75] Inventors: Holger B. Thomasen, Wallerod; Anne R. Eisenhardt, Birkerod, both of Denmark

[73] Assignee: Radiometer A/S, Copenhagen, Denmark

[21] Appl. No.: 273,110

[22] Filed: Nov. 16, 1988

Related U.S. Application Data

[63] Continuation of Ser. No. 144,734, Jan. 15, 1988, abandoned, which is a continuation of Ser. No. 908,973, Sep. 17, 1986, abandoned, which is a continuation of Ser. No. 670,159, Nov. 9, 1984, abandoned, which is a continuation of Ser. No. 397,242, Jul. 12, 1982, abandoned, which is a continuation of Ser. No. 171,011, Jul. 18, 1980, abandoned, which is a continuation of Ser. No. 28,076, Apr. 9, 1979, abandoned.

[30] Foreign Application Priority Data

Feb. 23, 1979 [DK] Denmark .............................. 809/79

[51] Int. Cl.$^4$ ..................... B08B 9/00; A06M 16/00
[52] U.S. Cl. ..................................... 134/18; 134/42; 435/264

[58] Field of Search ................... 134/18, 42; 252/91, 252/106, 135, 174.12, DIG. 12; 435/188, 264

[56] References Cited

U.S. PATENT DOCUMENTS

| | | | |
|---|---|---|---|
| 3,600,318 | 8/1971 | Mast ..................... | 252/DIG. 12 X |
| 3,655,570 | 4/1972 | Isono et al. ................ | 252/135 X |
| 3,753,915 | 8/1973 | Demange0n ........... | 252/DIG. 12 X |
| 3,860,484 | 1/1975 | O'Malley ............... | 435/188 |
| 3,860,536 | 1/1975 | Landwerlen et al. .......... | 435/188 X |
| 3,985,686 | 10/1976 | Barrat ................... | 252/174.12 X |
| 4,115,292 | 9/1978 | Richardson et al. ...... | 252/174.12 X |

OTHER PUBLICATIONS

Siggaard-Andersen, The Acid-Base Status of the Blood, 4th Edition, 1974, pp. 157-165.

*Primary Examiner*—W. Gary Jones
*Attorney, Agent, or Firm*—Bryan, Cave, McPheeters & McRoberts

[57] ABSTRACT

Subtilisin or subtilisin-like enzymes are used in rinse solutions for apparatus analyzing protein-containing biological liquids, such as blood analysis apparatus, to obviate measuring errors ascribable to protein deposits. A preferred rinse solution contains subtilisin, a borate buffer, and germicides.

12 Claims, No Drawings

METHOD FOR CLEANING INSTRUMENTS USED FOR ANALYZING PROTEIN-CONTAINING BIOLOGICAL LIQUIDS

This is a continuation of U.S. application Ser. No. 144,734 filed Jan. 15, 1988, which was a continuation of Ser. No. 908,873 filed Sept. 17, 1986, which was a continuation of Ser. No. 670,159 filed Nov. 9, 1984, which was a continuation of Ser. No. 397,242 filed July 12, 1982, which was a continuation of Ser. No. 171,011, filed July 18, 1980, which was a continuation of Ser. No. 028,076 filed Apr. 9, 1979, all of which applications are now abandoned.

FIELD OF THE INVENTION

The present invention relates to a process in operating apparatus analyzing protein-containing biological liquids and a composition for use in the process.

BACKGROUND OF THE INVENTION

Instruments analyzing biological liquids are in widespread use. Thus, blood, serum, or plasma analysis instruments in more or less automated form are indispensible in hospitals and laboratories where it is of importance to know values of such blood parameters as for example pH, $Pco_2$, $Po_2$, hemoglobin content, electrolyte concentration etc., and parameters derived therefrom, for example "standard bicarbonate". Nowadays, it is required that these parameters be determined with great exactitude, and in some clinical situations, for example during surgery, the exact and reliable determination of blood parameters may be of decisive importance. Therefore, it is required that these instruments show a high degree of accuracy and reliability.

Blood, serum or plasma analysis instruments (below termed "blood analysis instruments" for brevity) typically operate with alternation between an analysis procedure in which a sample is introduced into the apparatus for determination of one or more parameters, and a rinse procedure in which a rinse solution is passed through the instrument manually or automatically, either introduced the same was as the sample, or, especially for automatic instruments, introduced automatically from a rinse solution reservoir connected to the instrument. The normal duration of the rinse procedure is of the same order as the normal duration of each analysis procedure. With suitable intervals, a calibration procedure takes place in which the measuring units of the instrument are calibrated against calibration liquids or gases, followed by rinsing with the rinse solution. In certain types of instruments, the calibration is performed automatically with intervals programmed into the instrument.

In practical use of blood analysis instruments, it has been found that the instruments sometimes give a certain degree of measuring errors. It may be found that the actual read-out of the instrument deviates from the data of reference standard liquids, or that the response time for one or more of the measuring units becomes abnormally long. It is presumed that such problems are primarily due to deposits on the detection areas of the measuring units, especially deposits of proteins or proteinaceous substances or lipids from the blood samples analyzed in the apparatus.

BRIEF DESCRIPTION OF THE INVENTION

It has now been found that such measuring errors or stability problems in instruments analyzing protein-containing biological liquids, e.g. blood analysis instruments, can be prevented or minimized by performing the rinsing procedure of the instruments with a rinse liquid which contains, in dissolved state, subtilisin or a subtilisin-like enzyme.

As appears from the examples, the use of such a rinse solution minimizes the measuring errors or instability problems ascribable to protein and other deposits in measuring chambers and transport ducts of the instruments without impairing the accuracy of the instruments.

Conventional rinse solutions for blood analysis instruments typically consist of water or aqueous solutions of sodium chloride in physiological concentration and optionally containing germicides, and which are free of buffers and other constituents that might affect the measuring results. Various rinse solutions are commercially available and are typically marketed or prepared in portions sufficient for 1-2 week's normal use. According to the present invention it has been found possible to establish a subtilisin-containing rinse solution in which the subtilisin will retain a reasonable activity for a period of for example 2-3 weeks at room temperature, but which, on the other hand, in spite of the fact that it contains buffer, will not incur any errors in the measuring results.

DISCUSSION OF THE PRIOR ART

It is known to remove deposits in blood analysis instruments by means of a subtilisin-containing detergent solution (vide the Instruction manual for OSM2 Oxygen Saturation Meter from Radiometer A/S, Copenhagen, page 4, "Removal of Protein Deposits") but in this known method, the operation of the apparatus is stopped, the enzyme-containing detergent solution is introduced via the sample transport system of the instrument, and the solution is allowed to remain for 2 to 24 hours, whereafter the solution is removed, and the system is rinsed with distilled water.

This known use of subtilisin is conventional for such enzyme as it involves a long incubation time and is followed by rinsing with the enzyme-free distilled water prior to resuming the measurements.

It was also known to use a trypsin- and triethanolamine-containing standard and/or rinse solution in the operation of a flow-through blood calcium measuring system, confer "Instruction Manual model 99-20 serum calcium flow-thru system, Orion Research Incorporated, USA 1969, form IM99-20/966" and various literature discussions of the system, e.g.:

Hattner, R. S., Johnson, J. W., Bernstein: D. S., Wachman, A. and Brackman, J., "Electrochemical determination of apparent ionized serum calcium using a calcium-selective electrode: the method and values in normal humans and a comparison to total serum calcium", Clin. Chim. Acta. 28 (1970) 67–75.

Lindegärde, F. and Zettervall, O., "Serum ionized calcium in a normal population studied with a calcium ion-sensitive electrode", Israel J. Med. Sci., vol. 7, No. 3, March 1971.

Schwartz, H. D., McConville, B. C. and Christopherson, E. F., "Serum ionized calcium by specific ion electrode", Clin. Chim. Acta. 31 (1971) 97–197.

Ting-Kai Li and Piechocki, Joseph T., "Determination of serum ionic calcium with an ion-selective electrode: evaluation of methodology and normal values", Clinical Chemistry, vol. 17, No. 5, 1971, 411–416.

Fuchs, C., Paschen K., Spieckermann P. G. and Westberg, C. v., "Bestimmung des ionisierten Calciums im Serum mit einer.ionenselektiven Durchflasselektrode: Methodik und Normalwerte", Klinische Wochenschruft, 50. Jahrgang. 17. Heft, I. September 1972, 824–832.

Lindegärde, F., "Potentiometric determination of serum ionized in a normal human population", Clin. Chim. Acta, 40 (1972) 477–484.

Seamonds, Bette, Towfighi, Javad and Arvan, Dan A., "Determination of ionized calcium in serum by use of an ion-selective electrode", Clinical Chemistry, vol. 18, No. 2, 1972, 155–180.

Subryan, V. L., Popovtzer, M. M., Parks, S. D. and Reeve, E. B., "Measurement of serum ionized calcium with the ion-exchange electrode", Clinical Chemistry, vol. 18, No. 12, 1972, 1459–1482.

Ladenson, Jack H. and Bowers, George N., Jr., "Free calcium in serum. I. Determination with the ion-specific electrode, and factors affecting the results", Clinical Chemistry, 19, 565, 1973.

A more recent work describing the use of trypsin solutions in connection with calcium flow through electrodes is Cattrall, R. W. and Fong, Kwok-Tai, Talanta, Vol. 25, 1978, 541–543, according to which the sample arm of the calcium measurement system was flushed with destilled water containing 0.50% w.v of trypsin after each measurement.

However, as appears from the above-mentioned instruction manual, the trypsin-containing solutions have to be prepared fresh daily, and this would make their use cumbersome and unsuitable especially in connection with modern apparatus which, due to the high degree of automation, otherwise requires relatively little labor.

Furthermore, as appears from the below examples, it has surprisingly been found that even very low concentrations of subtilisin in the solutions of the present invention are far more efficient with respect to removing deposits after biological liquids than trypsin solutions of even much higher concentration. While the present invention is not to be limited to any theory, one of the reasons for the surprising efficiency of subtilisin for this purpose may be that subtilisin and subtilisin-like enzymes have no clear specificity (or otherwise expressed, are broad-spattered enzymes), and therefore more universally decompose the many different proteins which may be contained in the impurities to be removed. Another important feature of subtilisin in this connection is that it shows capability of decomposing ester bonds which may be of importance in the removal of lipid deposits in the instruments.

While the above-discussed known uses of trypsin-containing solutions are all connected to flow-through apparatus, i.e. apparatus in which the measurement is performed while the sample solution is passed through the measuring unit, it has been found, in accordance with the present invention, that the subtilisin-containing solutions may be used, without impairing the measured results, also in static measuring conditions, in which a volume of enzyme-containing rinse solution will necessarily be present as a reminiscence in the measuring chamber during the measurement.

DETAILED DESCRIPTION OF THE INVENTION

In accordance with conventional practice, the term "subtilisin-like enzymes" is intended to designate enzymes which, like subtilisin, are endopeptidases and have broad specificity, that is, are capable of rupturing peptide bonds between many different amino acids, in contrast to, for example, trypsin- and pepsin-like enzymes, which have a relatively narrow specificity and therefore are capable of rupturing a relatively small number of types of peptide bonds. For the purpose of the present invention, the preferred subtilisin-like enzymes are enzymes which, with respect to stability properties, resemble subtilisin, in other words, show good stability in solution.

With reference to the generally acknowledged international enzyme nomenclature system of 1972, the subtilisin-like enzymes are classified in class 3.4, especially in the sub-classes 3.4.22, 3.4.24 and 3.4.99 and in the sub-class to which the subtilisins pertain, that is 3.4.21, the contemplated enzymes in this sub-class being the ones with broad specificity in contrast to, for example, trypsin which also pertains to the sub-class.

Examples of specific enzymes which are contemplated to be useful for the purpose of the present invention, are 3.4.21.1 chymotrypsin A and B, 3.4.21.2 chymotrypsin C, 3.4.21.9 Acrosin, 3.4.21.11 Elastase, 3.4.21.14 the subtilisin classification comprising "Subtilisin Carlsberg" (also called Subtilisin A and B or Subtilopeptidase A and B), and BPN' (Nagarseproteinase), Subtilisin Novo and such similar enzymes produced by *Bacilius pumilis* and *Bacillus licheniformis*, 3.4.21.13 Phaseolus proteinase, 3.4.21.15 Aspergillus alkaline proteinase, 3.4.21.16 Alternaria endopeptidase, 3.4.21.17 Arthrobacter serine proteinase, 3.4.21.18 Tenebrio α-proteinase, 3.4.22.2 Papain, 3.4.22.5 Bromelain, 3.4.22.7 Asclepain, 3.4.22.9 Yeast proteinase 3, 3.4.24.2 Sepia proteinase and the commercial product "Pronase" which is available from BDH Chemicals Ltd., England, and which is a mixture containing several broad spectered proteinases.

The instrument operated in accordance with the method of the invention may be any apparatus analysing any parameter or constituent in blood or any other biological liquid and in which there is alternation between an analysis procedure and a rinse procedure, which in most practical cases means that immediately subsequent to analysis on a particular sample, a rinse procedure follows before the next sample is introduced and analysed. However, the scope of the present invention also extends to the cases where a number of samples are analyzed before a rinse procedure is performed. The normal duration of each rinse procedure is of the same order as the normal duration of each analysis procedure (normally the order of a few minutes or less), as distinguished from the conventional incubation with a subtilisin-containing solution mentioned above in the Discussion of the Prior Art. Examples of instruments which are suitably operated in accordance with the method of the invention are blood gas analyzers measuring pH, $P_{CO_2}$, and $P_{O_2}$, oxygen saturation meters, instruments for determining hemoglobin content, and instruments for determining the concentration of particular electrolytes in biological liquids, in particular blood. In the known art operation of such instruments, each analysis on a sample is typically followed by rinsing with a rinse solution taken from a reservoir connected to the apparatus.

Due to the limited stability of enzymes in solution, the enzyme-containing rinse solution of the invention will normally not be factory-produced, but will preferably be prepared by the end user by dissolving the enzyme in water or an aqueous solution. Preferably, a pH buffer buffering to a pH suitable for the enzyme, for subtilisin in the range of pH 7-9.5, is included in a low concentration at the same time, either in that the solution contains the buffer already, or in that the enzyme to be dissolved is contained in a composition which also contains a buffer substance.

The enzyme concentration in the rinse solution of the invention will normally be in the range of 0.05-50 Anson Units (AU) per liter, suitably in the range of 0.1-2.0, preferably 0.2-1.0, for example about 0.5 AU per liter for subtilisin, and the concentration of pH buffer, which may, for example, be a phosphate buffer, John-Lindsay universal buffer (citric acid, $H_3PO_3$, $KH_2PO_4$+veronal), or, preferably, a borate buffer, is preferably of the order of about $0.2 \times 10^{-3}M - 5 \times 10^{-3}M$, preferably $10^{-3}M - 4 \times 10^{-3}M$ and most preferably about $3 \times 10^{-3}M$ in the rinse solution. One feature of the invention is that it is possible to establish a sufficiently stable subtilisin-containing solution for normal use over a two weeks period, that is, the buffer capacity is sufficient to avoid such a pH lowering due to the $CO_2$ of the ambient air which would cause the stability and activity of the subtilisin to decrease to a too high extent, while at the same time the buffer capacity is sufficiently low to allow the rinse solution to be used in, for example, blood gas analysis equipment without any adverse influence on the pH and $P_{CO_2}$ measurements.

It has been found that the presence of suitable germicides increases the stability of the enzyme in the aqueous solution, and it is therefore preferred that the rinse solution contains one or more germicides which do not substantially decrease the activity of the enzyme. The germicides are usually present in a low, but still efficient concentration in the solution, typically a concentration of the order of 1-1000 ppm. A preferred germicide combination for use in the rinse solution is a combination of a bactericide and a fungicide. Specific germicides which have been found to be compatible with subtilisin in practice and to increase the stability thereof are didecyldimethylammonium bromide and trichloro-tert butyl alcohol which are preferably used in combination. Other examples of germicides for use in the solution of the invention are phenylmercuric nitrate and cupric chloride which may suitably be used in combination with a concentration of 1-5 ppm each.

A solution comprising an enzyme selected from the group consisting of subtilisin and subtilisin-like enzymes, a pH buffer, in particular a borate buffer, and a germicide is believed to be novel per se and constitutes an aspect of the present invention. In addition to its use in operating blood analysis apparatus in accordance with the method described above, such rinse solution, with or without a salt, preferably sodium chloride, to obtain a physiological ionic strength, can also be used for other rinsing and cleaning purposes, for example for rinsing or cleaning clinical equipment or other objects where it is of importance to effectively remove or prevent proteinaceous and/or lipid deposits.

A preferred composition of this invention is one which is adapted for dissolution in commercially available rinse solutions and which therefore contains the enzyme in dry form together with sufficient buffer substance to dry form to yield, on dissolution, the desired concentration of buffer and enzyme in the rinse solution to be used according to the invention.

Such composition is preferably packed in a closed container which may, for example, be a vial with pierceable septum, so that the composition is redissolved by injection of water or rinse solution injected from a syringe, withdrawn through the syringe and transferred to the portion of rinse solution for which it is adapted. The enzyme of such composition is preferably subtilisin, and the pH buffer preferably a borate buffer. The quantities of the enzyme and the borate buffer are adapted to the final volume of enzyme-containing rinse solution to be prepared.

The composition of the invention is preferably prepared by freeze drying an aqueous solution comprising the enzyme and the buffer and (vide below) optionally a germicide or a combination of germicides. The aqueous solution is suitably metered directly into the container in which it is to be packed, for example a vial, and is freeze-dried in situ. Apart from the dissolution and freeze-drying combination being a suitable way of dosing the enzyme with sufficient exactitude, the freeze-drying also has the advantage that it imparts to the buffer a voluminous structure which is very easily redissolved in water when the solution of the invention is made by reconstitution of the freeze-dried composition.

Another type of suitable unit dosage composition containing enzyme and optionally buffer is a porous body in which the enzyme and optionally buffer is absorbed in the porosities in solid state to be redissolved and leached out with water or aqueous solutions, for example, a porous plastic body or a porous body of a sintered inorganic material such as aluminum silicate/aluminum oxide. The porous bodies may, if desired, contain a ferromagnetic core so that they can be used as stirring bodies movable by an external magnetic field such as described in Danish patent application No. 2737/78. One suitable way of preparing porous bodies with absorbed enzyme is to immerse suitable porous bodies into a buffered enzyme solution, optionally with application of vacuum and subsequent release of the vacuum to obtain a better penetration into the porous body, and thereafter drying the thus impregnated body, suitably by freeze-drying. The porous bodies are suitably packed in air tight containers, preferably plastic "blister" packings.

The composition of the invention may further comprise a germicide to increase the storage stability of the composition. The germicide or germicides may either be present in the composition in a concentration corresponding to the desired end concentration of germicide in the final rinse solution, or, when the composition is used for dissolution in a rinse solution which already contains germicide, in a smaller concentration which merely serves to protect the composition proper against microbial deterioration prior to its dissolution. In accordance with what has been previously stated, a preferred germicide combination is a fungicide and a bactericide, and specific examples of suitable germicides are didecyldimethylammonium bromide, trichloro-tert butyl alcohol, phenylmercuric nitrate, and cupric chloride.

In the method of the invention, the rinsing or flushing using the enzyme-containing rinse solution is normally performed according to exactly the same routine as with the normal rinse solution adapted for the particular instrument in question.

EXAMPLE 1

An enzyme-containing rinse solution was prepared in the following manner.

To 1 liter of deionized water were added sodium chloride (analysis grade) to a concentration of 0.150M and tris-buffer (tris(hydroxymethyl)aminomethane) to a concentration of 0.001M. To the resulting solution was added 10 ml of a solution of 2 g/liter pure crystalline subtilisin (subtilisin A from Novo Industri A/S, Copenhagen, activity 25 Anson units (AU) per g) in deionized water, which solution had been freshly prepared on the same day.

The resulting enzyme-containing rinse solution was used as the rinse solution in the automated rinse procedure subsequent to each blood analysis in two automatic blood gas instruments (ABL1 from Radiometer A/S, Copenhagen). Donor blood was used as the samples analyzed. Per day about 25 injections of blood samples and, correspondingly, 25 subsequent automatic rinsing procedures plus frequently (about once per hour) automatic calibration with subsequent passage of rinse solution took place. During the periods (for example in the evening and overnight) in which no analyses were performed, the instruments made their normal automatic calibration procedure about once an hour with subsequent rinsing.

Each instrument contains two liquid sensors, and the voltage from these liquid sensors was determined as a basis for the assessment of the contamination-preventing effect obtained by the addition of enzyme to the rinse solution, as it is presumed that any reduction in the output voltage is caused by contamination of the detection area of the liquid sensor. After two weeks' operation using the rinse solution prepared as described above, the instruments were operated for further two weeks with rinse solution prepared in the same manner, but with omission of the subtilisin.

A unilateral t test on the liquid sensor voltages recorded shows that significantly better purification (higher liquid sensor voltage) was obtained for 3 of the 4 built-in liquid sensors through the addition of enzyme, while there was no significance for higher voltge for the 4th liquid sensor (but, on the other hand, not any significance for lower voltage). According to experience, samples of donor blood do not incur the same contamination problems as are encountered in the practical use of the instruments, because blood from sick patients generally has a much higher tendency to contaminate than blood from sound persons, and especially, some individual blood samples from sick patients may give extraordinarily troublesome contamination in the instrument.

EXAMPLE 2

A rinse solution was prepared in the same manner as described in Example 1. The stock solution was a few days old and contained such an amount of Subtilisin A in a 0.001M tris buffer in deionized water that 2 ml of the solution contains 10 mg of subtilisin A. In a hospital, this rinse solution was compared with a rinse solution without enzyme content in operation of a blood gas analysis instrument ABL2 from Radiometer A/S, Copenhagen. The apparatus performs automatic rinsing and calibration procedures in the same way as described in Example 1. Prior to the application of the enzyme-containing rinse solution, the transient difference for the pH electrode of the instrument, expressed as the difference between first data read-out containing the voltage of the pH electrode after introduction of a new sample and the third data read-out for the same sample, was unsatisfactorily high: 0.017 ±0.066, expressed as pH. The individual results corresponding to this over a period appear from the below table. After introduction of the enzyme-containing rinse solution, this difference decreased to 0.007±0.0015. However, after one week, it increased slightly to 0.009±0.003 which is believed to be due to a decreased enzyme activity which is probably ascribable to the fact that the stock solution which did not contain germicides had already been a few days old prior to the preparation of the rinse solution and had been subject to air transportation.

| With rinse solution without enzyme | | With the enzyme-containing rinse solution | |
|---|---|---|---|
| Date | ΔpH | Date | ΔpH |
|  | 0.015 | 3/11 | 0.010 |
|  | 0.011 | 3/11 |  |
|  | 0.012 |  | 0.010 |
| 1/11 | 0.020 | 3/11 | 0.007 |
| 1/11 |  | 4/11 | 0.007 |
| 1/11 | 0.013 | 4/11 | 0.005 |
|  | 0.028 | 4/11 | 0.005 |
|  | 0.029 | 4/11 | 0.005 |
| 3/11 | 0.020 | 4/11 | 0.005 |
| 3/11 | 0.016 | 4/11 | 0.005 |
| 3/11 | 0.017 | 4/11 | 0.005 |
|  | 0.014 | 6/11 | 0.009 |
|  |  |  | 0.003 |
|  |  | 6/11 | 0.005 |
|  |  | 7/11 | 0.009 |
|  |  |  | 0.016 |
|  |  |  | 0.010 |
|  |  |  | 0.005 |
|  |  |  | 0.005 |
|  |  |  | 0.005 |
|  |  |  | 0.012 |
|  |  | 9/11 | 0.005 |
|  |  |  | 0.003 |
|  |  |  | 0.013 |
|  |  | 9/11 | 0.009 |

EXAMPLE 3

A rinse solution was prepared in the same manner as described in Example 2, the stock solution used in this case having been stored in frozen state between its preparation and its use. The rinse solution was used in hospital operation of a blood gas analysis instrument ABL2 from Radiometer A/S, Copenhagen. Prior to the use of the enzyme-containing rinse solution, a rinse solution without any enzyme content was used, and the apparatus showed an error in the read-out of the hemoglobin measuring unit, the read-out on a standard without any content of hemoglobin being 1 g% hemoglobin. About 12 hours subsequent to introduction of the subtilisin-containing rinse solution in the instrument, the read-out of the hemoglobin measuring unit became 0 g% on the above-mentioned standard, and this value was retained throughout the week in which the subtilisin-containing rinse solution was used. As the subtilisin-containing rinse solution was thereafter exchanged with the usual rinse solution, the hemoglobin measuring unit read-out on the standard without hemoglobin again rose to about 1 g%.

EXAMPLE 4

Prescriptions for Enzyme Compositions According to the Invention

1. One unit dosage of the enzyme composition is adapted for being dissolved in ½ liter rinse solution which is 0.150M with respect to sodium chloride and which contains 0.003% of "Deciquam 222" from Struers, Copenhagen (didecylaimethylammonium bromide) and 0.1% of trichloro-tert.butyl alcohol. The unit dosage consists of 0.25 AU subtilisin A (From Novo Industri A/S, Copenhagen), 0.16 g $Na_2B_4O_7.10H_2O$ (corresponding to a final concentration of $0.84\times10^{-3}M$ in the rinse solution which corresponds to a borate concentration of $3.4\times10^{-3}M$), $12\times10^{-5}$ g Deciquam 222 and $4\times10^{-3}$ g trichloro-tert.butyl alcohol.

This composition is prepared in the following manner:

1 kg of deionized water, 10 g of KCl, analysis grade, 0.03 g of Deciquam 222, 1 g of trichloro-tert.butyl alcohol and 40 g of $Ka_2B_4O_7.10H_2O$ are dissolved, and thereafter, 62.5 AU of subtilisin A is added. Stirring is performed until complete dissolution has been obtained. The solution is sterile-filtered, and portions of 4 ml of the solution are transferred into sterile vials. The solution is freeze-dried under sterile conditions at $-45°$ C. for 3-4 hours, whereafter the vials are dried for 15 hours at $8\times10^{-2}$ mm Hg. Subsequently, the vials are closed, still under sterile conditions, with rubber septum and metal ring.

In the use of the composition, 5 ml of the above-mentioned rinse solution is injected into the vial by means of a syringe, whereafter the vial is shaken carefully. The mixture is aspirated back into the syringe and transferred to the bottle of rinse solution immediately before the rinse solution is to be used.

2. In a solution of 10 g of Subtilisin A per 100 ml water buffered with 1M borate buffer At pH 8, porous cylinders prepared from aluminum silicate/aluminum oxide and having a length of 10 mm, a diameter of 5 mm and showing a porosity of 30% were immersed. The cylinders were allowed to remain in the liquid for about 10 minutes whereafter they were removed from the liquid and air dried at room temperature. The cylinders treated in this manner showed an acitivity of 0.05 AU per cylinder, which is 28% of the theoretical value.

The same procedure was repeated, but this time with application of vacuum on the liquid with the cylinders. After 10 minutes, the vacuum was released.

EXAMPLE 5

An investigation was made of the capability of subtilisin and trypsin, respectively, to remove deposits in glass tubes through which blood had been passed for a long period.

100 capillary tubes (diameter 1.25 mm, length 126 mm) half filled with blood, were rotated so that the blood volume constantly passed from one half of the tube to the other half of the tube.

After 85 hours of treatment in this manner, the tubes were flushed very thoroughly, first with water and thereafter with 0.150M NaCl solution.

On about 40 tubes, the end showed a deposit which had not been removed by the flushing.

These contaminated tubes were divided into three portions with about 12 tubes in each portion. The capillary tubes were filled with and thereafter immersed into rinse liquids with the following composition:

A. 20 mg crystalline subtilisin A Novo per liter $3\times10^{-3}M$ $Na_2B_4O_7.10H_2O$ 0.15M NaCl pH-7

B. 660 mg crystalline trypsin (Sigma No. T-8253) $3\times10^{-3}M$ triethanolamine 0.150M NaCl pH-7

C. 0.0150M NaCl

Rinse solution B corresponds, with respect to content of trypsin and triethanolamine, to the known standard solution used for calcium flow-through systems.

After standing 10 hours in the rinse solutions, the tubes were thoroughly flushed with 0.150M NaCl.

The visual assessment gave the following results:

| Rinse Solution | Result |
| --- | --- |
| A. | Very slight deposit is noted on a few of the tube ends. |
| B. | A distinct deposit is visible on almost all the tube ends. |
| C. | Distinct deposits are seen on all tube ends. |

The protein deposits remaining on the capillary tube ends after the enzyme treatment were stained with amido blue (which stains proteins). It was very easy to see that the ends of the tubes treated with rinse solution A had much less staining than the ends of the tubes treated with rinse solutions B, and C, respectively.

In order to obtain a quantitative spectrophotometric determination, the concentration of amido blue released within a certain period was measured for each group of tubes.

All tubes were thoroughly flushed with sodium chloride solution and cut into a length of 4 cm. Thereafter they were all filled with sodium chloride solution, and the stained deposits were removed by means of a piece of steel which was moved by means of an exterior magnet. After two hours' treatment in this manner, the liquid was poured out from the tubes and diluted to 3 ml for each group of tubes. The extinction of each diluted solution was determined on a spectrophotometer at 650 nm using 0.150M NaCl as a reference. The results were as follows:

| Rinse Solution | Extinction | Relative Extinction |
| --- | --- | --- |
| A Subtilisin | 0.0025 | 1 |
| B Trypsin | 0.019 | 20 |
| C 0.150 M NaCl | 0.137 | 55 |

According to Lambert-Beers' law, extinction and substance concentration are proportional ($E=A\times C\times 1$), which means that this spectrophotometric measurement also confirms that much larger amounts of protein remain in the tubes rinsed with trypsin than in the tubes rinsed with subtilisin.

EXAMPLE 6

In order to assess the influence of the enzyme-containing rine solutions on the analysis results obtained in blood gas analysis equipment, 4 Radiometer ABL2 blood gas analysis instruments were operated with a normal rinse solution consisting of a 0.150M aqueous NaCl solution, and 4 ABL2 instruments were operated with a subtilisin A-containing rinse solution (a 0.150M aqueous NaCl solution containing 1 mM Tris buffer and 0.50 AU/liter of subtilisin A, pH 8.8). After about 72 hours of operation, all of the instruments were used for analysis on the same batch of blood, 5 blood measurements being performed per apparatus. A unilateral variance analysis showed tht there as no difference between pH measured on the instruments using the normal rinse solution and the instruments using the subtilisin-containing rinse solution.

In another experiment, it was investigated whether the above-mentioned subtilisin A-containing rinse solution, when used in an ABL2 blood gas measuring instrument, influenced the following analyses, measured on precision standards:

pH $Pco_2$ $Po_2$

The standards were injected into the ABL2 instrument partly during a period in which it was rinsed with the above-mentioned normal rinse solution and partly during a period in which the instrument was rinsed with the subtilin A-containing rinse solution.

A unilateral variance analysis showed that the values of the above blood parameters measured on the instrument were not dependent on the rinse solution used.

The above-reported two experiments show that the subtilisin- and buffer-containing rinse solution according to the invention does not impair the accuracy of the measurements.

I claim:

1. A method for rinsing an instrument used for analyzing blood, plasma or serum to determine blood parameters selected from the group of pH, $Pco_2$, $Po_2$, hemoglobin content, oxygen saturation, electrolyte concentration, and parameters derived therefrom, to minimize measuring errors or stability problems ascribable to deposits on the detection areas of the instruments, consisting essentially of passing through measuring chambers and transport ducts of the instrument a rinse solution so as to remove deposits from previous samples; said rinse solution containing an effective amount of an enzyme selected from the group consisting of subtilisin and other endopeptidases having broad specificity; the normal duration of the rinsing operation being a few minutes or less.

2. A method of operating a blood analysis instrument used for analyzing blood, plasma or serum to determine blood parameter selected from the group of pH, $Pco_2$, $Po_2$, hemoglobin content, oxygen saturation electrolyte concentration, and parameters derived therefrom, to minimize measuring errors or stability problems ascribable to deposits on the detection areas of the instrument, consisting essentially of alternating between an analysis procedure in which a sample to be analyzed is introduced into the instrument and is analyzed in the instrument and a rinse procedure in which a rinse solution is passed through measuring chambers and transport ducts of the instrument to remove deposits from previous samples; the normal duration of each rinse procedure being a few minutes or less; and the rinse procedure being performed with a rinse solution containing an effective amount of an enzyme selected from the group consisting of subtilisin and other endopeptidases having broad specificity.

3. A method as claimed in either claim 1 or 2, wherein the concentration of enzyme is 0.05–50 AU per liter.

4. A method as claimed in 3, wherein the concentration of enzyme is 0.1–2.0 AU per liter.

5. A method as claimed in either claim 1 or 2, wherein the rinse solution contains a pH buffer.

6. A method as claimed in claim 5, wherein the rinse solution contains a salt in a concentration resulting in an ionic strength of the solution which is of the same level as the ionic strength of blood.

7. A method as claimed in claim 6, wherein the salt is sodium chloride in a concentration of about 0.150 mole/liter.

8. A method as claimed in claim 7, wherein the rinse solution contains one or several germicides which do not substantially decrease the activity of the enzyme.

9. A method as claimed in claim 8, wherein the rinse solution contains trichlorobutane.

10. A method as claimed in claim 8, wherein the rinse solution contains a combination of didecyldimethylammoniumbromide and trichlorobutanol.

11. A method as claimed in claim 10, wherein the concentration of didecyldimethylammoniumbromide is about 0.003%, and the concentration of trichlorobutanol is about 0.1%.

12. A method as claimed in claim 5, wherein the pH buffer is a borate buffer.

* * * * *

UNITED STATES PATENT AND TRADEMARK OFFICE
CERTIFICATE OF CORRECTION

PATENT NO. : 4,867,797  Page 1 of 4

DATED : September 19, 1989

INVENTOR(S) : HOLGER B. THOMASEN et al.

It is certified that error appears in the above-identified patent and that said Letters Patent is hereby corrected as shown below:

Column 1, line 45:  Change "was" to --way--.

Column 2, line 68:  Change "97-197" to --97-107--.

Column 3, line 8-9:  Change "Durchflasselektrode" to --Durchflusselektrode--.

Column 3, line 10:  Change "Wochenschruft" to --Wochenschrift--. After "Jahrgang" change period (.) to comma (,). After "Heft," change "I" to --1--.

Column 3, line 18:  Change "155-180" to --155-160--.

Column 3, line 22:  Change "1459-1482" to --1459-1462--.

Column 3, line 32:  Change "w.v" to --w/v--.

Column 3, line 51:  Change "spattered" to --spectered--.

Column 4, line 24:  Change "the" to --this--.

Column 4, line 39:  After "Yeast proteinase" change "3," to --B,--.

Column 5, line 57:  Change "per se" to --*per se*--.

Column 6, line 23:  Change "in situ" to --*in situ*--.

Column 6, line 41-42:  Change "patent application" to --Patent Application--.

Column 8, line 6:  Change "$\pm$ 0.066" to --$\pm$ 0.006--.

UNITED STATES PATENT AND TRADEMARK OFFICE
CERTIFICATE OF CORRECTION

PATENT NO. : 4,867,797

DATED : September 19, 1989

INVENTOR(S) : HOLGER B. THOMASEN et al.

It is certified that error appears in the above-identified patent and that said Letters Patent is hereby corrected as shown below:

Column 8, lines 22-43, that portion on the right of the chart reading

| $\Delta pH$ |  | $\Delta pH$ |
|---|---|---|
| 0.010 | should read | 0.010 |
| 0.010 |  | 0.010 |
| 0.007 |  | 0.007 |
| 0.007 |  | 0.007 |
| 0.005 |  | 0.006 |
| 0.005 |  | 0.006 |
| 0.005 |  | 0.005 |
| 0.005 |  | 0.006 |
| 0.005 |  | 0.008 |
| 0.005 |  | 0.008 |
| 0.009 |  | 0.009 |
| 0.003 |  | 0.008 |
| 0.005 |  | 0.008 |
| 0.009 |  | 0.009 |
| 0.016 |  | 0.016 |
| 0.010 |  | 0.010 |
| 0.005 |  | 0.006 |
| 0.005 |  | 0.009 |
| 0.005 |  | 0.006 |
| 0.012 |  | 0.012 |
| 0.005 |  | 0.006 |
| 0.003 |  | 0.008 |
| 0.013 |  | 0.013 |
| 0.009 |  | 0.009 |

UNITED STATES PATENT AND TRADEMARK OFFICE
CERTIFICATE OF CORRECTION

PATENT NO. : 4,867,797

DATED : September 19, 1989

INVENTOR(S) : HOLGER B. THOMASEN et al.

It is certified that error appears in the above-identified patent and that said Letters Patent is hereby corrected as shown below:

Column 9, line 9: Change "didecylaimethylammonium" to --didecyldimethylammonium--.

Column 9, line 39: Change "At" to --at--.

Column 9, line 58: Change "126" to --125--.

Column 10, line 4: Change "pH-7" to --pH∼7--.

Column 10, line 5: Change "B. 660 mg" to --B. 600 mg--.

Column 10, line 6: Change "pH-7" to --pH∼7--.

Column 10, line 7: Change "C. 0.0150M" to --C. 0.150M--.

Column 10, line 11: Change "10 hours" to --16 hours--.

Column 10, line 45-50, that portion of chart reading

| Extinction | | Extinction |
|---|---|---|
| 0.0025 | should read | 0.0025 |
| 0.019 | | 0.049 |
| 0.137 | | 0.137 |

Column 10, line 53: Change "(E = A x C x 1)" to --(E = $\lambda$ x C x 1)--.

UNITED STATES PATENT AND TRADEMARK OFFICE
CERTIFICATE OF CORRECTION

PATENT NO. : 4,867,797

DATED : September 19, 1989

INVENTOR(S) : HOLGER B. THOMASEN et al.

It is certified that error appears in the above-identified patent and that said Letters Patent is hereby corrected as shown below:

Column 10, line 60: Change "rine" to --rinse--.

Column 11, line 3: Change "tht" to --that--.

Column 11, line 39: Between "through" and "measuring", there should be --the--.

Column 12, line 3: "parameter" should read --parameters--.

Column 12, line 4: After "saturation", there should be a comma (,).

Column 12, line 12: Between "through" and "measuring", there should be --the--.

Signed and Sealed this

Twenty-second Day of September, 1992

*Attest:*

DOUGLAS B. COMER

*Attesting Officer*   *Acting Commissioner of Patents and Trademarks*